(12) United States Patent
Goto (10) Patent No.: US 8,663,238 B2
(45) Date of Patent: Mar. 4, 2014

(54) TREATMENT TOOL

(75) Inventor: Hiroaki Goto, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 805 days.

(21) Appl. No.: 12/105,011

(22) Filed: Apr. 17, 2008

(65) Prior Publication Data

US 2008/0300454 A1 Dec. 4, 2008

(30) Foreign Application Priority Data

May 31, 2007 (JP) ................................. 2007-144873

(51) Int. Cl.
*A61B 17/24* (2006.01)
*A61B 8/14* (2006.01)
*A61B 10/00* (2006.01)
*A61B 18/18* (2006.01)

(52) U.S. Cl.
USPC ............. 606/113; 600/466; 600/564; 606/32; 606/46

(58) Field of Classification Search
USPC ............ 606/32, 37–41, 45–50, 113; 600/372, 600/466, 471, 564
See application file for complete search history.

(56) References Cited

U.S. PATENT DOCUMENTS

| 3,910,279 | A | | 10/1975 | Okada et al. |
| 4,582,067 | A | | 4/1986 | Silverstein et al. |
| 4,708,137 | A | * | 11/1987 | Tsukagoshi ..................... 606/46 |
| 6,077,274 | A | | 6/2000 | Ouchi et al. |
| 6,514,248 | B1 | | 2/2003 | Eggers et al. |
| 7,357,801 | B2 | * | 4/2008 | Burbank et al. ................. 606/45 |
| 7,585,298 | B2 | * | 9/2009 | Kawahara et al. .............. 606/45 |
| 2004/0092953 | A1 | | 5/2004 | Salameh et al. |
| 2004/0133232 | A1 | | 7/2004 | Rosenbluth et al. |

FOREIGN PATENT DOCUMENTS

| DE | 86 26 340 | 3/1990 |
| JP | 8-509894 | 10/1996 |
| JP | 2000-262539 A | 9/2000 |
| JP | 2002-263111 A | 9/2002 |
| JP | 2004-073582 | 3/2004 |
| WO | WO 94/26013 | 11/1994 |
| WO | WO 99/09857 | 3/1999 |
| WO | WO 2004/075732 A2 | 9/2004 |
| WO | WO 2006/053308 A2 | 5/2006 |

OTHER PUBLICATIONS

Japanese Office Action dated Feb. 21, 2012 from corresponding Japanese Patent Application No. JP 2007-144873.

* cited by examiner

*Primary Examiner* — Linda Dvorak
*Assistant Examiner* — Brian M Antiskay
(74) *Attorney, Agent, or Firm* — Scully, Scott, Murphy & Presser, P.C.

(57) ABSTRACT

A treatment tool used with an endoscope includes a flexible sheath having an internal insertion through hole which extends in the axial direction of the sheath; one or more holes that are placed in a distal end portion of the sheath, and that penetrate a wall portion of the sheath so as to allow the insertion through hole to communicate with the outside of the sheath; a wire that passes from the insertion through hole in the sheath through the hole portion so that a portion thereof is exposed to the outside of the sheath; and a wire restricting portion that is provided in the vicinity of at least one hole portion from among the one or more hole portions, and that prevents the wire which is passing through the hole portion and extending to the outside of the sheath from shifting from the radial direction of the sheath.

7 Claims, 11 Drawing Sheets

TREATMENT TOOL

BACKGROUND OF THE INVENTION

1. Field of the Invention

The present invention relates to a treatment tool that is used in conjunction with an endoscope.

Priority is claimed on Japanese Patent Application No. 2007-144873, filed May 31, 2007, the contents of which are incorporated herein by reference.

2. Description of Related Art

Conventionally, a treatment tool that is used in conjunction with an endoscope, for example, an incision tool that is used to incise biological tissue is known in which, normally, wires which form a knife portion are housed inside a flexible sheath or else are positioned alongside an outer surface of the circumferential wall of the flexible sheath. When the biological tissue is actually to be incised, a portion of each wire is made to expand diametrically so as to protrude some distance from the outside of the flexible sheath. In this state, an incision is performed by pressing the wires against a predetermined position of the biological tissue which is to be incised while supplying high-frequency current to the wires (see Published Japanese Translation No. 8-509894 of the PCT International Publication, and Japanese Unexamined Patent Application, First Publication No. 2004-73582).

However, in a conventional treatment tool in which the wires are expanded when an incision is to be made, when a portion of the wires is expanded to make an incision, the problem has arisen that the wires become twisted or bent and cannot be expanded to a desired shape, which has resulted in the incision direction being unstable. Particularly when this expansion is accompanied by a rotational movement of the wires, the wires collapse so that there is a possibility that the operation will not be completed.

SUMMARY OF THE INVENTION

The treatment tool according to the present invention is a treatment tool that is used in conjunction with an endoscope and includes: a flexible sheath having an internal insertion through hole which extends in the axial direction of the flexible sheath; one or more hole portions that are placed in a distal end portion of the flexible sheath, and that penetrate a wall portion of the flexible sheath so as to allow the insertion through hole to communicate with the outside of the flexible sheath; a wire that passes from the insertion through hole in the flexible sheath through the hole portion so that a portion thereof is exposed to the outside of the flexible sheath; and a wire restricting portion that is provided in the vicinity of at least one hole portion from among the one or more hole portions, and that prevents the wire which is passing through the hole portion and extending to the outside of the flexible sheath from shifting from the radial direction of the flexible sheath.

In the treatment tool of the present invention, it is also possible for a guide portion whose width is larger than an outer diameter of the wire to be formed in the wire restricting portion, and for the wire restricting portion to be mounted on the flexible sheath such that the wire which passes through the hole portion passes continuously through the guide portion.

In the treatment tool of the present invention, it is also possible for the wire to be an incision knife

DETAILED DESCRIPTION OF THE INVENTION

Embodiments of the present invention will now be described with reference made to the drawings.

First Embodiment

Figure 1:
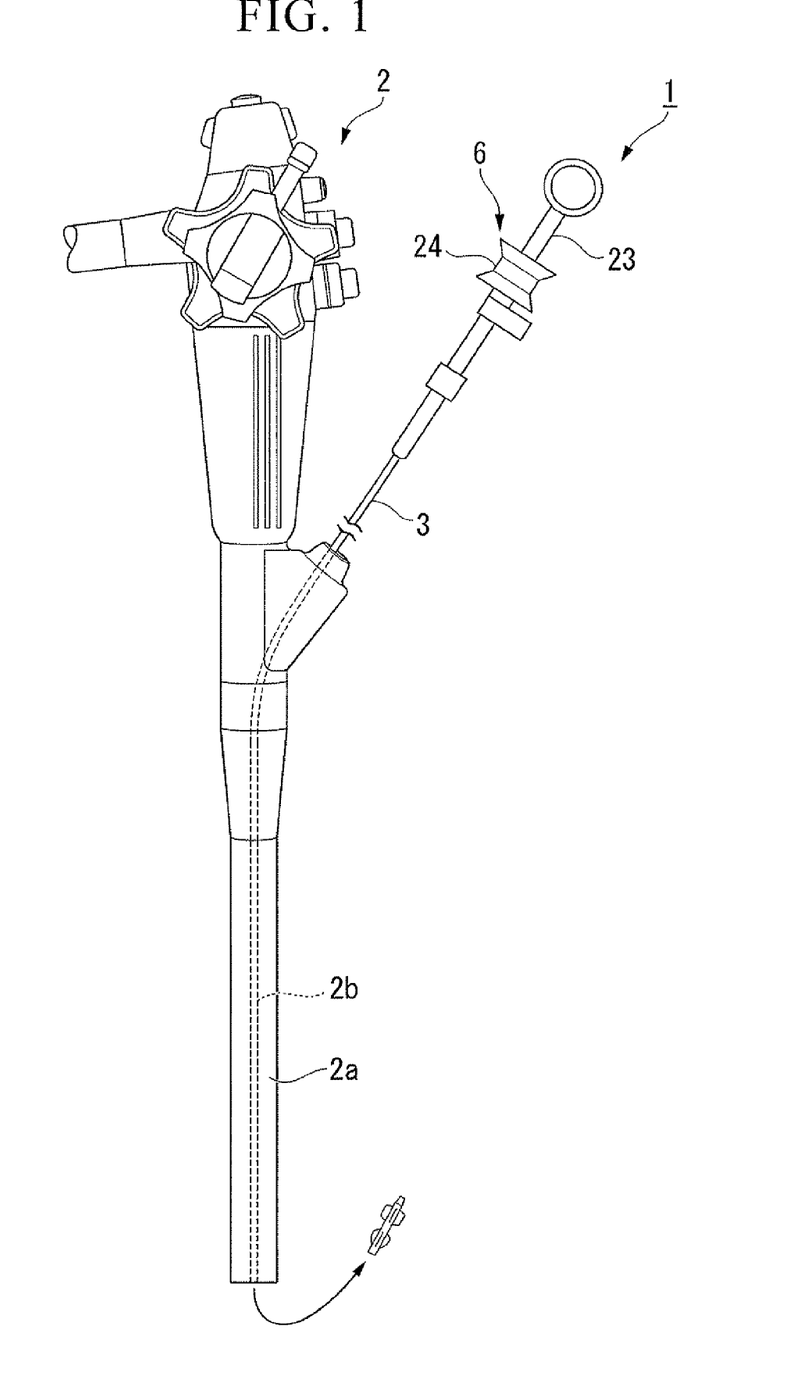
FIG. 1 is a perspective view showing a state in which a treatment tool according to an embodiment of the present invention is fitted onto an endoscope.
Figure 2:
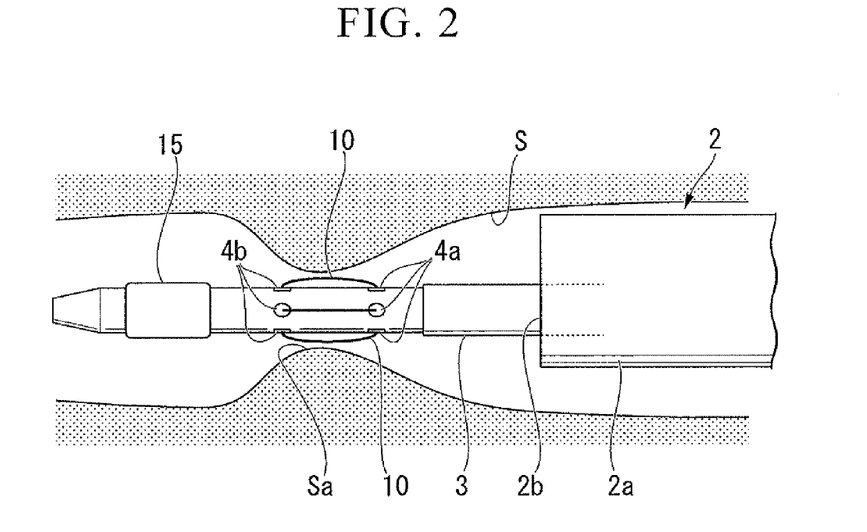
FIG. 2 is a side view showing a distal end of this treatment tool.
Figure 3:
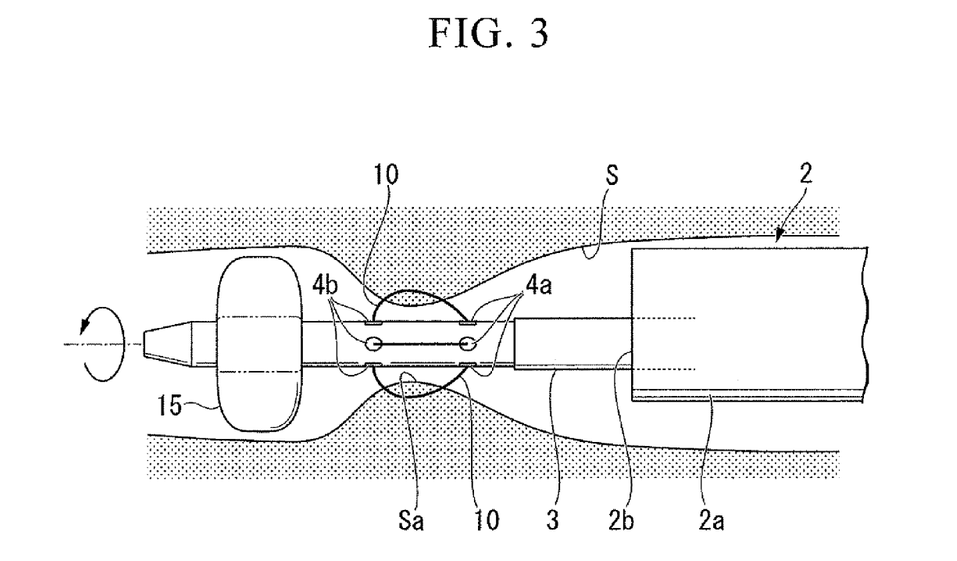
FIG. 3 is a cross-sectional view showing a state in which a narrowing portion of an esophagus is incised by this treatment tool.

FIGS. 1 to 8B show an embodiment of an incision tool which is an example of a treatment tool according to the present invention. In these drawings, FIG. 1 is a perspective view showing a state in which an incision tool is fitted into an endoscope, FIG. 2 is a cross-sectional view illustrating a state when the incision tool is inserted into an esophagus, and FIG. 3 is a cross-sectional view illustrating a situation in which a narrowing portion of an esophagus is incised by the incision tool.

As is shown in FIG. 1, an incision tool 1 of this embodiment is used by being incorporated into an endoscope 2. As is shown in FIGS. 1 and 2, the incision tool 1 is provided with: a flexible sheath 3 that is formed by, for example, a coil sheath which has an internal insertion through hole 3a extending along its axis and that has sufficient flexibility to allow it to be inserted into a treatment tool channel 2b which is formed in an insertion portion 2a of the endoscope 2; a plurality of wires 5 that are inserted through the interior of the flexible sheath 3 and that form wire exposed portions 10 which are exposed on the outside of the flexible sheath 3 as a result of a portion thereof being inserted through first wire insertion through holes (i.e., hole portions) 4a that are provided in a distal end portion of the flexible sheath and through second wire insertion through holes (i.e., hole portions) 4b that are provided on the flexible sheath distal end side of the first wire insertion through holes 4a; and an operating unit 6 that is connected to one end side (i.e., a base end side) of the wires 5 and that adjusts the length of the exposed portions 10 of the wires which are exposed on the outside of the flexible sheath by moving forwards or backwards relatively to the flexible sheath 3 in the longitudinal direction of the wires 5.

Note that, here, the side of the incision tool 1 where the operating unit 6 is located is referred to as the base end side, while the opposite side therefrom is referred to as the distal end side.

Here, a first wire insertion through hole 4a and a second wire insertion through hole 4b that are formed in the flexible sheath 3 and through which the plurality of wires 5 are respectively inserted is formed for each one of the wires 5. That is, the same number of first wire insertion through holes 4a and second wire insertion through holes 4b are formed as the number of wires 5. Here, the first wire insertion through holes 4a are formed at the same position in the longitudinal direction of the flexible sheath 3, and the second wire insertion through holes 4b are also formed at the same position in the longitudinal direction of the flexible sheath 3. Moreover, these first and second wire insertion through holes 4a and 4b are formed at equidistant intervals in the circumferential direction.

Figure 4:
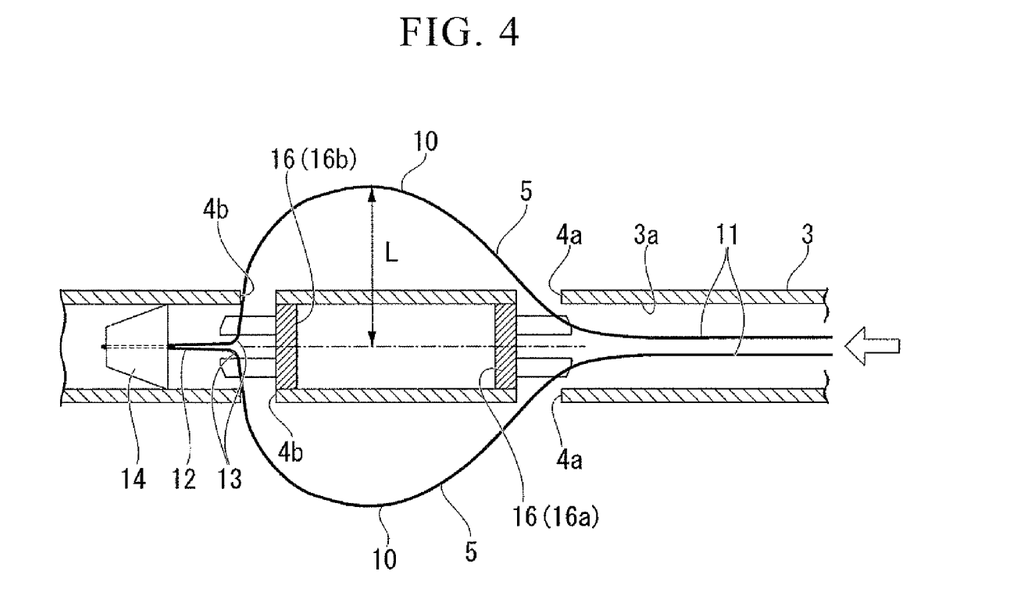
FIG. 4 is a cross-sectional view showing an internal portion of a flexible sheath at a distal end of this treatment tool.
Figures 5A, 5B:
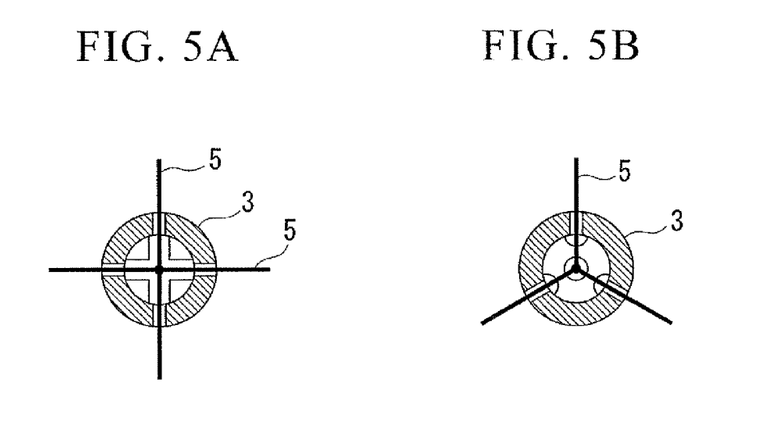
FIGS. 5A to 5D are front views showing examples of the layout of exposed portions of wires of this treatment tool.
Figure 5C:
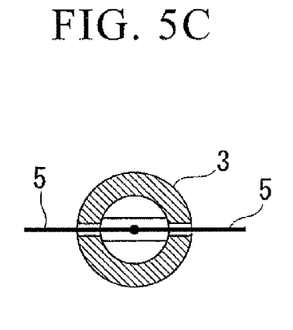
Figure 5D:
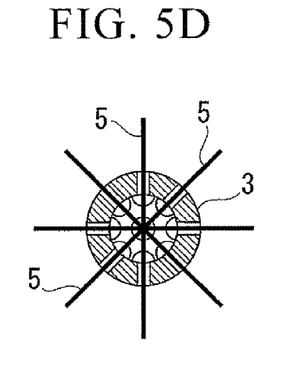
Figure 5E:
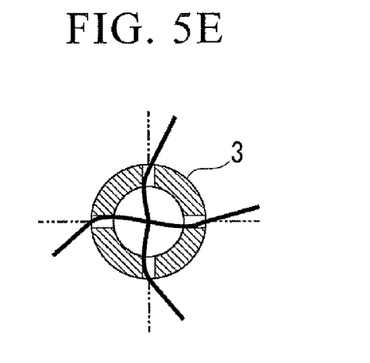
FIG. 5E is a front view showing a reference example of exposed portions of wires illustrated to provide a comparison for the present invention.

As is shown in FIG. 4, the plurality of wires 5 each have a base end side insertion portion 11 that is inserted into the internal space of the flexible sheath 3 on the base end side of the first wire insertion through hole 4a, the exposed portion 10 that extends from this base end side insertion portion 11 towards the distal end side and passes through the first wire insertion through hole 4a so as to be exposed on the outside of the flexible sheath 3, a distal end side insertion portion 12 that extends from this exposed portion 10 towards the distal end side and passes through the second wire insertion through hole 4b so as to enter again into the internal space of the flexible sheath 3, and a bent portion 13 that is provided in an end portion on the exposed portion 10 side of the distal end side insertion portion 12 and that bends the wire 5 in the axial direction of the flexible sheath 3 from the direction in which it enters into the internal space of the flexible sheath 3 via the second wire insertion through hole 4b. Moreover, the plurality of wires 5 are bound together into a single bundle by a binding component 14 on the distal end side of the bent portions 13.

The wires 5 are flexible and, as is shown in FIG. 2 and FIG. 3, when the operating unit 6 is moved forwards or backwards in the longitudinal direction of the wires, the shape of the exposed portions 10 is deformed so as to expand towards the outer side or to contract towards the inner side. Moreover, the wires 5 are conductive so that, when they are supplied with a high-frequency current, they function as a knife portion in which the exposed portions 10 incise biological tissue (specifically, an inner esophageal wall).

The wires 5 are inserted through a hole in the center of the binding component 14, and the engagement of the wires 5 with the binding component 14 is fixed by frictional force generated by the elasticity of the binding component itself or by an adhesive agent or the like. The binding component 14 is formed in a tapered shape which narrows towards its distal end side from a material having suitable elasticity and heat resistance. The maximum outer diameter of the binding component 14 is set to a slightly larger value than that of the inner diameter of the flexible sheath 3. As a result, the binding component 14 is engaged by a suitable frictional force with the inner surface of the flexible sheath 3.

A balloon 15 that can be inflated to a larger diameter than that of the flexible sheath 3 is mounted on the distal end side of the flexible sheath 3 beyond the exposed portions 10 of the wires. The balloon 15 is connected to an air supply via an air tube (not shown) that is located within the flexible sheath. When air is supplied into the balloon 15 through this air tube, then, as is shown in FIG. 3, the balloon is inflated outwards.

As is shown in FIGS. 5A through 5D, the number of wires 5 may be 4, 3, 2, or 8, or any plural number other than these. However, as is shown in these drawings, the exposed portions 10 of the wires are placed at equidistant angular intervals in the circumferential direction so as to radiate outwards.

Heat resistant coating processing is performed on the vicinity of the first wire insertion through holes 4a and the second wire insertion through holes 4b of the wires 5. As a result, heat from the wires 5 does not get directly transmitted to stabilizers 16 (described below).

Figure 6A:
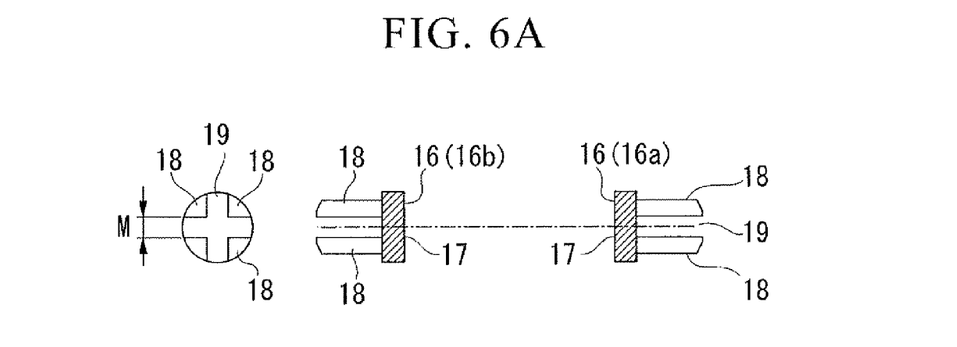
FIGS. 6A to 6C are views showing examples of a stabilizer used in this treatment tool.
Figure 6B:
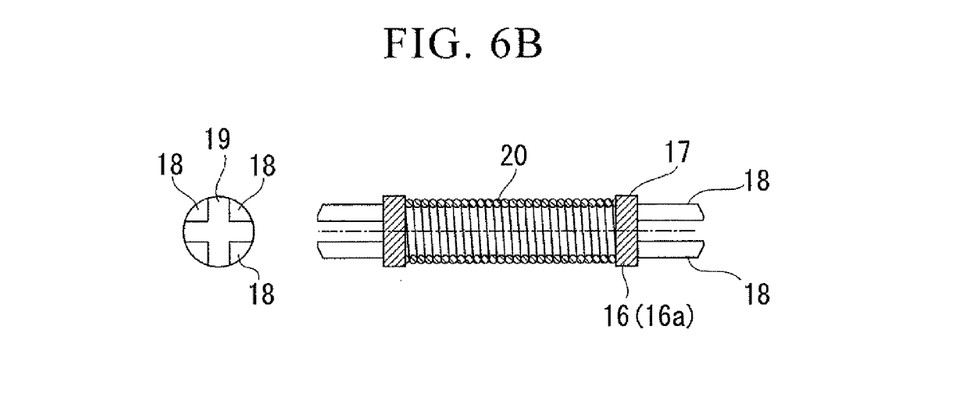
Figure 6C:
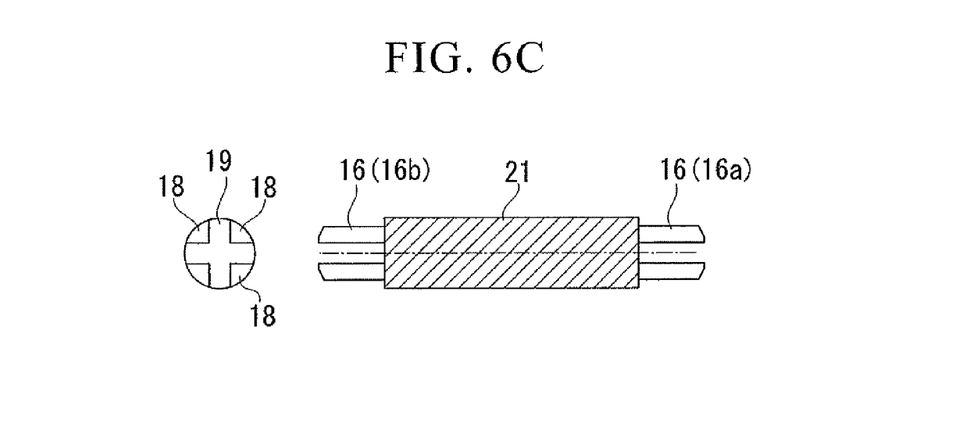

As is shown in FIGS. 6A to 6C, stabilizers (i.e., wire restricting portions) 16 that restrict movement of the wires 5 such that the wires 5 extend in a normal direction relative to the outer surface of the flexible sheath 3 without twisting to the left or right, in other words, such that they do not diverge from the radial direction of the flexible sheath 3 when the exposed portions 10 of the wires 5 are expanded are provided in the vicinity of first and second wire insertion through holes 4a and 4b inside the flexible sheath 3.

As is shown in FIGS. 6A to 6C and 7A to 7C, various types of stabilizers 16 can be considered. Note that in the examples of stabilizers 16 shown in these drawings, the number of wires 5 is four. For example, in the stabilizers shown in FIGS. 6A and 7A, stabilizers 16a and 16b that correspond to the first and second wire insertion through holes 4a and 4b both have the same configuration, and are placed on the inside of the flexible sheath 3 so as to be mutually symmetrical. They are fixed in position by a suitable fixing device such as an adhesive agent or by press-insertion or the like.

That is, the stabilizer 16a on the base end side which corresponds to the first wire insertion through holes 4a is formed by a circular plate portion 17, and by four protruding portions 18 having a fan-shaped cross section that extend from one side of the circular plate portion 17 in a direction which is perpendicular to the circular plate portion 17. These protruding portions 18 are fixed in position so as to face towards the base end side. The stabilizer 16b on the distal end side which corresponds to the second wire insertion through holes 4b is also formed by a circular plate portion 17, and by four protruding portions 18 having a fan-shaped cross section that extend from one side of the circular plate portion 17 in a direction which is perpendicular to the circular plate portion 17. In the distal end side stabilizer 16b, the protruding portions 18 are fixed in position so as to face towards the distal end side.

Wire guide grooves (i.e., guide portions) 19 are formed respectively between each protruding portion 18. The stabilizers 16a and 16b are fixed in position inside the flexible sheath 3 such that these wire guide grooves 19 have the same angular position as each other in the stabilizer 16a on the base end side and the stabilizer 16b on the distal end side, and also such that the wire guide grooves 19 each match the first and second wire insertion through holes 4a and 4b. The diameter of the wire guide grooves 19 is set as a slightly larger value than that of the diameter of the wires 5.

Distal ends of the protruding portions 18 are tapered so that the wires 5 can be speedily guided into the wire guide grooves 19. Note that the stabilizers 16a and 16b are manufactured from a material having a suitable rigidity such as, for example, metal or hard plastic.

Figure 7A:
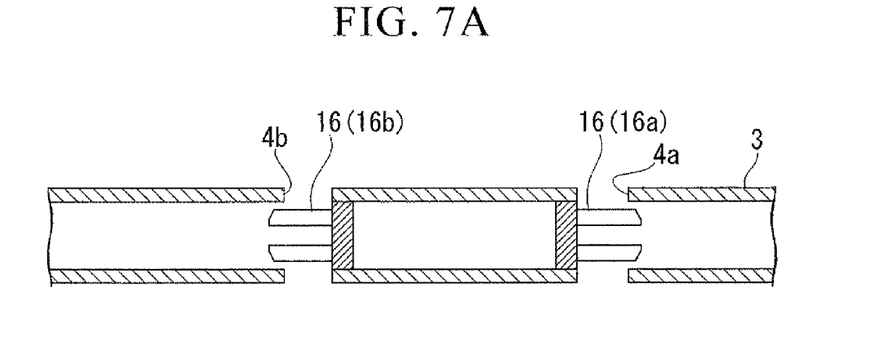
FIGS. 7A to 7C are cross-sectional views showing states in which the stabilizer shown in FIGS. 6A to 6C is fitted inside a flexible sheath.
Figure 7B:
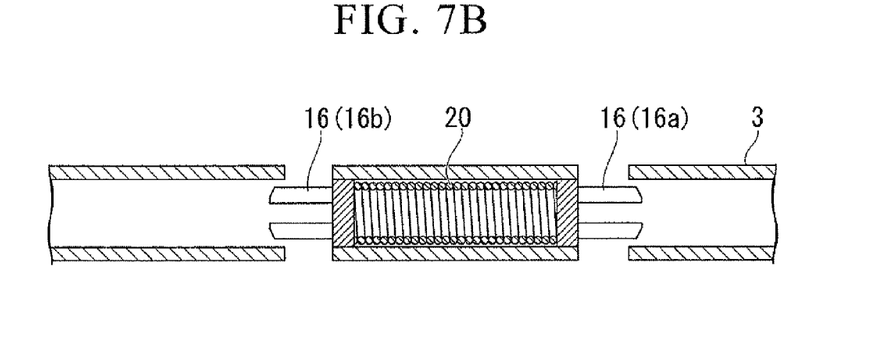

FIG. 6B and FIG. 7B show a state in which the base end side stabilizer 16a and the distal end side guide portion 16b are fixed in advance to both ends of a flexible linking coil 20, and these stabilizers 16a and 16b are fixed in a predetermined position inside the flexible sheath 3 as a single unit in a state in which they have been assembled in advance with the linking coil 20.

Figure 7C:
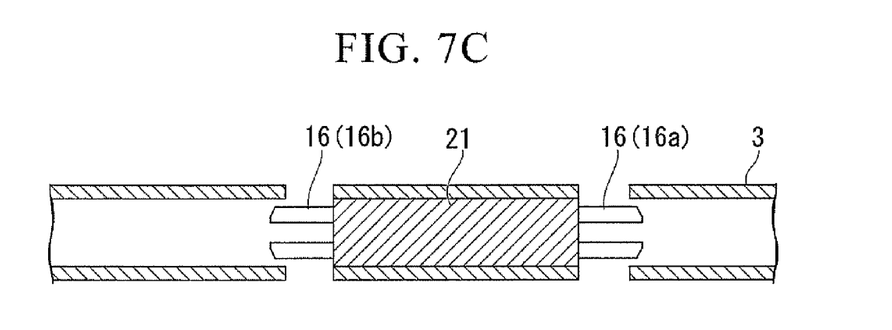

FIG. 6C and FIG. 7C show the base end side stabilizer 16a and the distal end side stabilizer 16b fixed in advance to both ends of a linking tube 21 that is formed from a soft plastic material such as, for example, PFTE, and these stabilizers 16a and 16b are fixed in a predetermined position inside the flexible sheath 3 as a single unit in a state in which they have been assembled in advance with the linking tube 21.

Figure 8A:
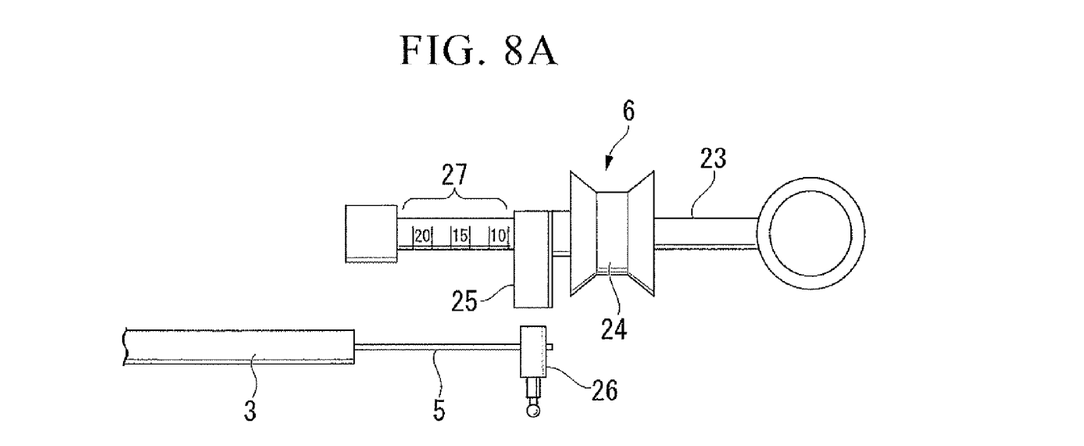
FIG. 8A is an exploded side view of an operating portion used in this treatment tool.
Figure 8B:
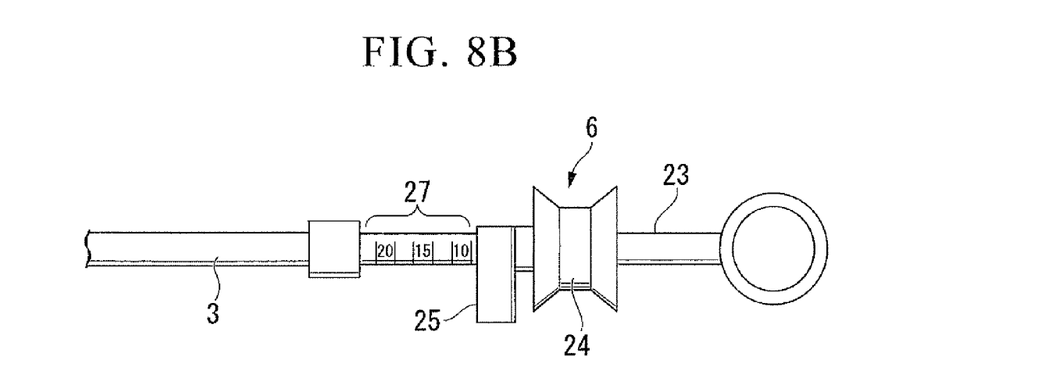
FIG. 8B is a side view of an operating portion used in this treatment tool.

FIG. 8A is an exploded view of the operating unit, while FIG. 8B is a side view of the operating unit. As is shown in these drawings, a base end side of the flexible sheath 3 is connected to an operating unit main body 23. Guide grooves (not shown) are formed extending in the axial direction in an intermediate portion of the operating unit man body 23. A sliding portion 24 that slides along the guide grooves is fitted onto the operating unit main body 23. A terminal supporting portion 25 is provided integrally with the sliding portion 24 and an electrode terminal 26 is mounted on this terminal supporting portion 25. A base end of the wire 5 is connected to the electrode terminal 26, and a connection terminal (not shown) that extends from a high-frequency power supply is able to be connected to the electrode terminal 26.

A gradation scale (i.e., index) 27 is formed on the operating unit main body 23. The distance moved by the sliding portion 24 and, consequently, a rough guide of a clearance L between the exposed portions 10 of the wires and the axis of the flexible sheath are displayed by means of this gradation scale 27 (see FIG. 4).

Here, if the sliding portion 24 is moved forwards or backwards in the longitudinal direction of the wires 5, the base end sides of the wires 5 that are connected to the electrode terminal 26 that moves integrally with the sliding portion 24 move in the same direction, so that the movement of the wires is transmitted sequentially to the distal end side. As a result, as is shown in FIG. 4, the length of the exposed portion 10 of the wires is adjusted. That is, the operating unit main body 23 and the sliding portion 24 form the operating unit 6 which adjusts the length of the exposed portions 10 of the wires by moving the wires 5 forwards or backwards.

Next, an operation to incise a narrowing portion of an esophagus using an incision tool having the above described structure will be described.

Firstly, as is shown in FIG. 2, the exposed portions 10 of the wires are placed in a state of maximum contraction, and the balloon 15 is left in a deflated state. Next, the insertion portion 2a of the endoscope 2 is perorally inserted and guided into the interior of an esophagus S until a narrowing portion Sa is confirmed by means of endoscopic images. Once the location of the narrowing portion Sa has been confirmed, the flexible sheath 3 is inserted into the treatment tool channel 2b of the endoscope 2 as is shown in FIG. 1. The flexible sheath 3 is then made to protrude from the distal end of the insertion portion 2 while this operation is being confirmed by means of endoscopic images.

Next, as is shown in FIG. 2, the exposed portions 10 of the wires are moved opposite the narrowing portion S of the esophagus while the operation is being viewed using endoscopic images. Adjustments to the movement of the exposed portions 10 of the wires to a position opposite the narrowing portion S of the esophagus are made by adjusting the insertion amount of the insertion portion 2a of the endoscope while the interrelationship between the endoscope and the treatment tool is kept the same. Alternatively, it is also possible to leave the insertion state of the insertion portion 2a of the endoscope unchanged, and adjust the amount of protrusion of the flexible sheath 3 from the distal end of the insertion portion 2a.

After the exposed portions 10 of the wires have been moved opposite the narrowing portion Sa of the esophagus in this manner, as is shown in FIG. 3, the sliding portion 24 of the operating unit 6 is moved forwards in the longitudinal direction of the wires, so that the exposed portion 10 of each wire is expanded outwards. At the same time as this, air is supplied via an air tube (not shown) to inflate the balloon 15.

Here, when the sliding portion 24 is moved forwards in the longitudinal direction of the wire, the base end sides of the wires 5 which are connected to the sliding portion 24 move in the same direction, so that this movement of the wires 5 is sequentially transmitted to the distal end side. As a result, the distal end sides of the wires 5 receive force moving them forwards. At this time, the bent portions 13 are provided on the wire distal end side insertion portions 12, so that the transmitted force of the wire movement is divided by the bent portions 13. That is, on the distal end side of the wires, the bent portions 13 function as stoppers so that forward movement of the wires on the forward side of the bent portions 13 is restricted. In addition, in this embodiment, forward movement of the wires on the forward side of the bent portions 13 is also restricted by the binding component 14 which is provided as an auxiliary component. As a result, movement of the base end side of the wires 5 relative to the flexible sheath 3 is concentrated in the exposed portions 10 of the wires that are exposed to the outside of the flexible sheath 3 so that, as is shown in FIG. 3, the exposed portions 10 of the wires expand to the desired shape.

Here, the operation to expand the exposed portions 10 of the wires using the operating unit 6 and the operation to inflate the balloon 15 can be linked together and performed simultaneously.

For example, it is also possible to employ a structure in which, when the sliding portion 24 of the operating unit 6 is moved forwards, this movement of the sliding portion 24 is detected by a sensor and, based on this detection result, an air supply device (not shown) is operated so that a predetermined quantity of air is supplied to the balloon 15 inflating the balloon 15.

Moreover, the stabilizers 16 are provided in the vicinity of the first wire insertion through holes 4a and the second wire insertion through holes 4b in the flexible sheath 3, and the exposed portions 10 of the wires 5 are guided by the wire guide grooves 19 in the stabilizers 16. Because of this, when the exposed portions 11 of the wires 5 expand, as is shown in FIGS. 5A through 5D, the exposed portions 10 of the wires 5 expand such that they extend in a normal direction relative to the outer surface of the flexible sheath 3. Accordingly, the exposed portions 10 of the wires 5 can be prevented from being twisted to the left or right as they expand in the manner shown in FIG. 5E, and they expand so as to radiate outwards while remaining positioned at equidistant angles in the circumferential direction. As is described below, this state is maintained in the same way while the treatment tool 1 is being rotated and the narrowing portion Sa in the esophagus is being incised.

When the exposed portions 10 of the wires have expanded to the desired shape, the clearance L between the exposed portions 10 of the wires and the flexible sheath axis can be accurately ascertained based on the gradation scale 27 formed on the operating unit main body 23. Because of this, when the operating unit 6 is being operated, it is possible to prevent in advance the incision depth to which the exposed portions 10 of the wires incise the narrowing portion Sa of the esophagus becoming deeper than is necessary.

When the operating unit 6 is operated causing the exposed portions 10 of the respective wires to expand, this operation is performed while high-frequency current is supplied to the wires 5. Accordingly, when the exposed portions 10 of the wires are expanded, the incision is made to a predetermined position inside the narrowing portion Sa of the esophagus. Subsequently, the treatment tool 1 is rotated together with the entire insertion portion 2a of the endoscope 2 while the high-frequency current is being supplied to the wires 5. This enables the narrowing portion Sa of the esophagus to be incised. Note that it is also possible for the incising of the narrowing portion Sa of the esophagus to be achieved by only rotating the treatment tool 1 instead of rotating the entire insertion portion 2a of the endoscope.

At this time, because the balloon 15 has been inflated at a predetermined position on the distal end side of the exposed portions 10 of the wires, even if force is applied unintentionally in the extraction direction during the rotation, the inflated balloon 15 functions as an anchor portion so that the position of the treatment tool 1 does not get shifted towards the base end side in the axial direction. That is, the exposed portions 10 of the wires are held in a position facing the narrowing portion Sa of the esophagus.

Moreover, as is described above, because the balloon 15 has been inflated at a predetermined position on the distal end side of the exposed portions 10 of the wires so that the distal end portion of the flexible sheath 3 is held in a substantially concentric position inside the esophagus by the balloon 15, it is possible to prevent the distal end portion of the flexible sheath which includes the exposed portions 10 of the wires being unintentionally shaken when the treatment tool is rotated. As a result, a smooth incision of the narrowing portion Sa of the esophagus can be performed by the exposed portions 10 of the wires.

After the incision, the balloon 15 is deflated and the exposed portions 10 of the wires are contracted by operating the operating unit 6. In this state, the distal end portion of the treatment tool 1 is retracted entirely within the channel in the endoscope, and the treatment tool 1 is extracted to the outside of the body together with the endoscope.

Second Embodiment

Figure 9:
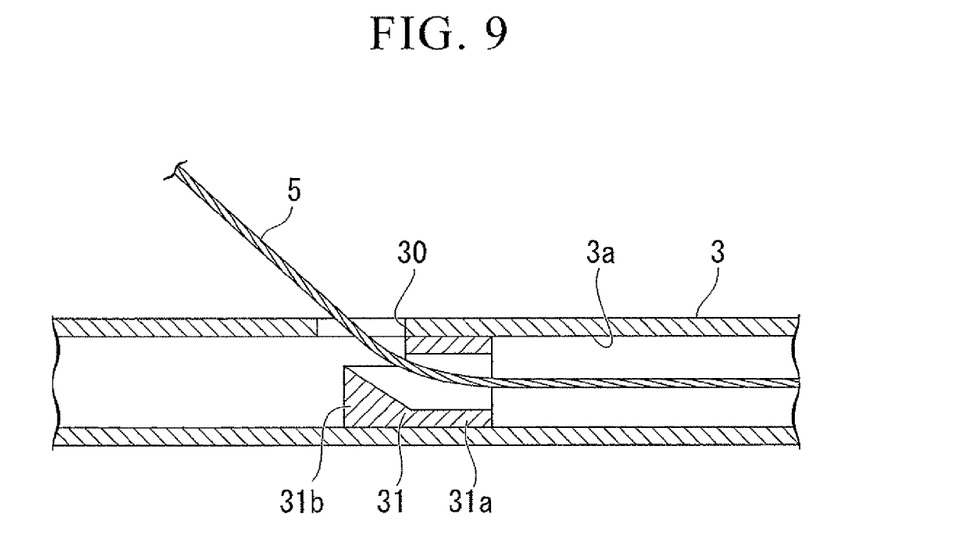
FIG. 9 is a cross-sectional view showing principal portions of a second embodiment of the present invention.
Figure 10:
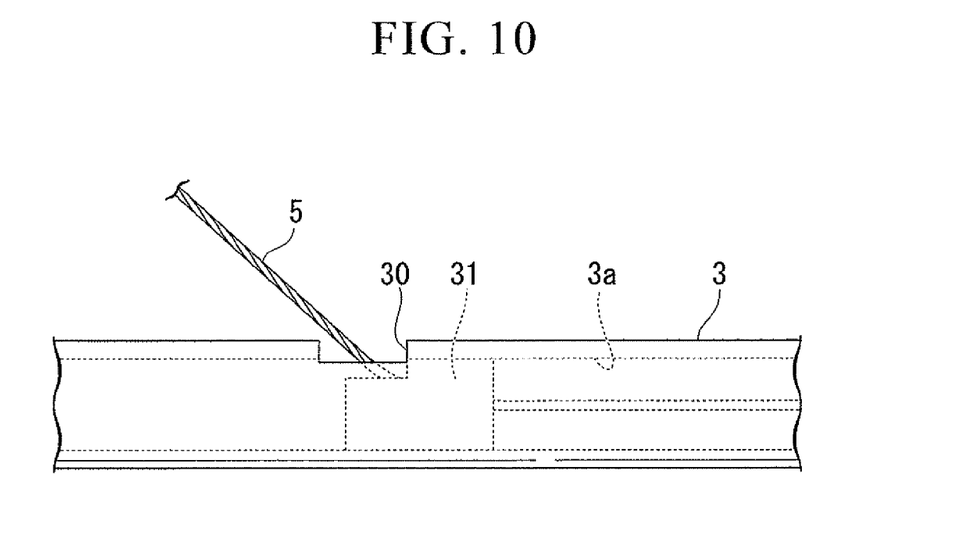
FIG. 10 is a side view of the second embodiment.

FIG. 9 and FIG. 10 show a second embodiment of the present invention. FIG. 9 is a cross-sectional view showing principal portions thereof, while FIG. 10 is a side view showing principal portions thereof. Note that, in order to simplify the description, component elements in the second embodiment that are the same as component elements described in the first embodiment are given the same symbols and a description thereof is omitted. This also applies in the third through fifth embodiments described below.

In this embodiment, only one wire insertion through hole (i.e., hole portion) 30 is provided in the flexible sheath 3, and the distal end side of only one single wire 5 passes through the insertion through hole 3a and is exposed to the outside of the flexible sheath 3 through this wire insertion through hole 30. The distal end of the wire 5 may be left floating unattached from the wire insertion through hole 30, or may be anchored by being connected to a jig (not shown) that is provided at the distal end of the flexible sheath 3, or it may be anchored by being connected directly to the distal end of the flexible sheath 3.

A stabilizer (i.e., a wire restricting portion) 31 that restricts movement of the wire 5 such that the wire 5 does not shift from the radial direction of the flexible sheath 3 when the exposed portion 10 of the wire 5 is being expanded is placed in the vicinity of the wire insertion through hole 30 inside the flexible sheath 3. The stabilizer 31 is provided with a cylindrical portion 31a that is fixed to an inner surface of the flexible sheath 3 so as to be adjacent to the wire insertion through hole 30, and a guide portion 31b that is integrally connected to the cylindrical portion 31a and that guides a wire passing through the interior of the cylindrical portion to the wire insertion through hole 30.

In the treatment tool of this second embodiment as well, the same effects are obtained as in the treatment tool of the above described first embodiment. That is, when the distal end of the wire 5 in the insertion through hole 3a is being exposed to the outside through the wire insertion through hole 30 or when the exposed wire distal end portion is being rotated, the wire 5 does not become twisted or bent, and it can be held in a desired shape.

Third Embodiment

Figure 11:
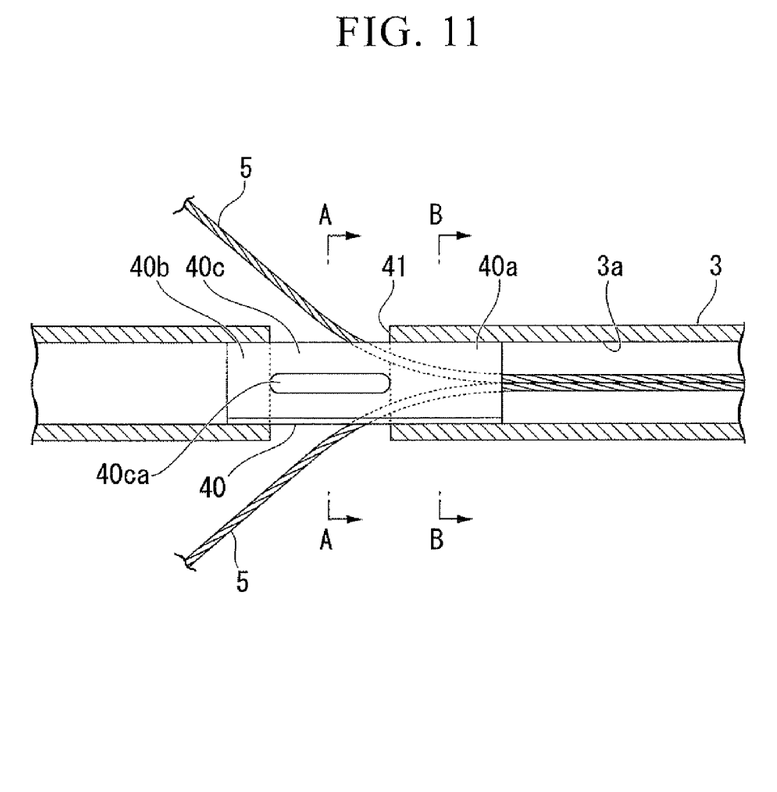
FIG. 11 is a cross-sectional view showing principal portions of a third embodiment of the present invention.
Figure 12A:
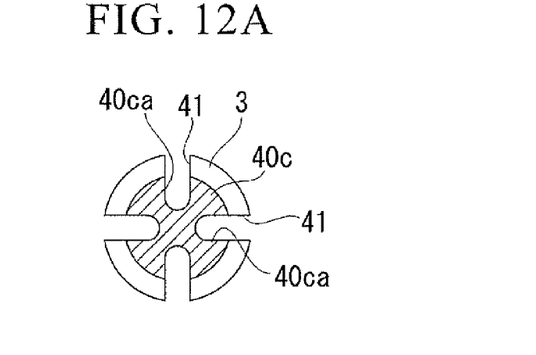
FIG. 12A is a cross-sectional view taken along a line A-A in FIG. 11.
Figure 12B:
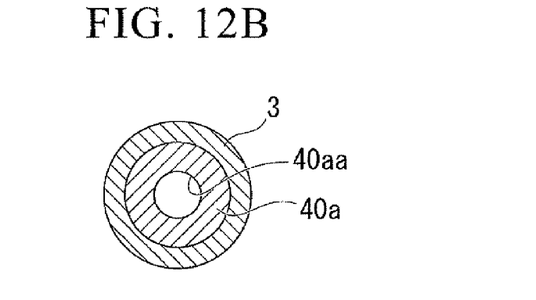
FIG. 12B is a cross-sectional view taken along a line B-B in FIG. 11.

FIG. 11 and FIGS. 12A and 12B show a third embodiment of the present invention. FIG. 11 is a cross-sectional view showing principal portions thereof FIG. 12A is a cross-sectional view taken along a line A-A in FIG. 11, and FIG. 12B is a cross-sectional view taken along a line B-B in FIG. 12A.

In this third embodiment, a stabilizer (i.e., a wire restricting portion) 40 having a different shape from the stabilizer shown in the above described first embodiment is used.

That is, the stabilizer 40 shown here is provided with a base end side base portion 40a and a distal end side base portion 40b that are provided a predetermined distance apart longitudinally, and a slit rail portion 40c which is provided between these two base portions. This stabilizer 40 is inserted into the insertion through hole 3a of the flexible sheath 3, and the base end side base portion 40a and the distal end side base portion 40b are each fixed using a suitable fixing device such as an adhesive agent or the like respectively to a portion in the vicinity of the base end side and a portion in the vicinity of the distal end side, which portions are on the internal surface of the insertion through hole 3a, while sandwiching wire insertion through holes 41 such that the slit rail portion 40c matches the wire insertion through holes 41.

As is shown in FIG. 12A, guide grooves (i.e., guide portions) 40ca that correspond to the wire insertion through holes 41 of the flexible sheath 3 are formed in the outer circumference of the slit rail portion 40c. The same number of guide grooves 40ca are formed as the number of wire insertion through holes 41. Here, the groove width of the guide grooves 40ca is set so as to be substantially the same as the inner diameter of the wire insertion through holes 41. These guide grooves 40ca are connected to a wire insertion through hole 40aa that is formed in the center of the base end side base portion 40a.

In the treatment tool of this third embodiment as well, in addition to the same effects as in the treatment tool of the above described first embodiment being obtained, because the guide grooves 40ca match the wire insertion through holes 41, the effect is obtained that guiding the wires can be performed even more smoothly.

Fourth Embodiment

Figure 13:
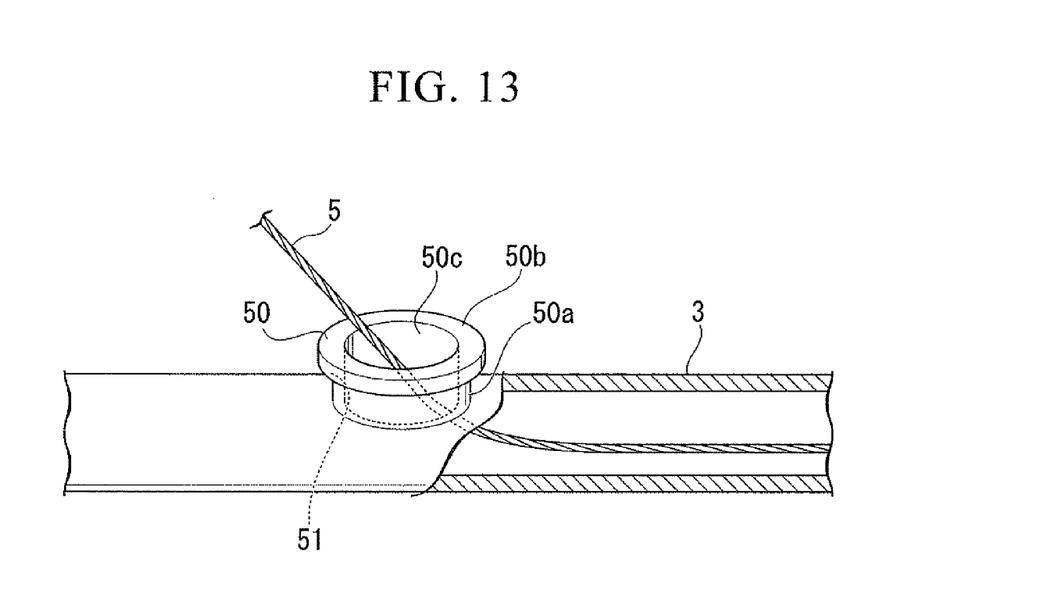
FIG. 13 is a perspective view of a fourth embodiment of the present invention in which a portion is shown in cross section.

FIG. 13 is a perspective view showing a fourth embodiment of the present invention with a portion thereof being shown in cross section.

A stabilizer (i.e., a wire restricting portion) 50 which is used in this fourth embodiment is set in position by being inserted from the outer side of a flexible sheath 3 into a wire insertion through hole 51 which is formed in this flexible sheath 3.

That is, the stabilizer 50 of this embodiment is formed by an insertion portion 50a whose outer diameter is set substantially equal to the inner diameter of the wire insertion through hole 51, and a protruding rim portion 50b that is mounted co-axially on a top end of this insertion portion 50a and whose diameter is larger than that of the insertion portion 50a. A wire guide hole (i.e., guide portion) 50c that guides a wire 5 which is inserted therethrough is formed in center portions of both the insertion portion 50a and the protruding rim portion 50b.

In the treatment tool of this fourth embodiment as well, in addition to the same effects as in the treatment tool of the above described first embodiment being obtained, because the stabilizer 50 is set in position by being inserted from the outside of the flexible sheath 3, the effect is obtained that setting the stabilizer in position is greatly simplified.

Fifth Embodiment

Figure 14A:
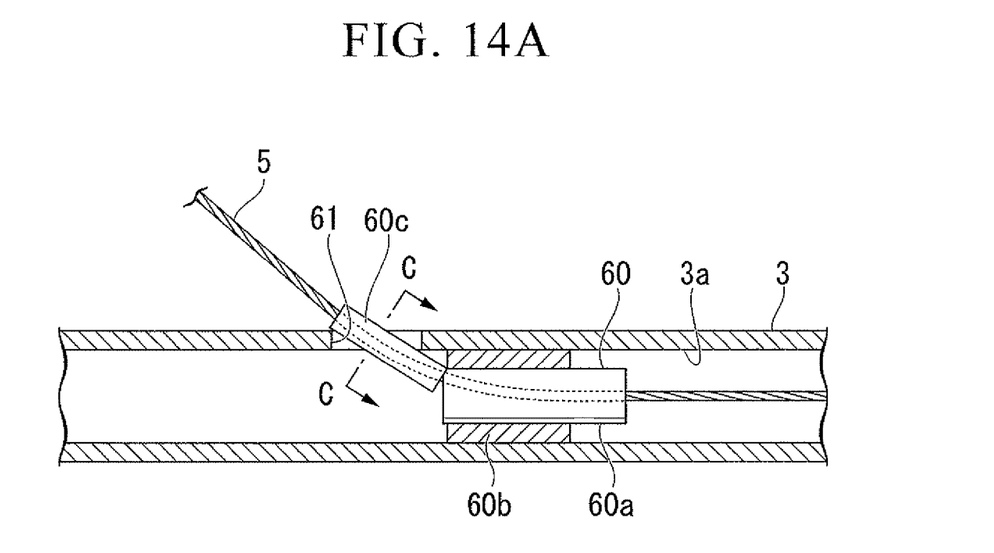
FIG. 14A is a cross-sectional view showing principal portions of a fifth embodiment of the present invention.
Figure 14B:
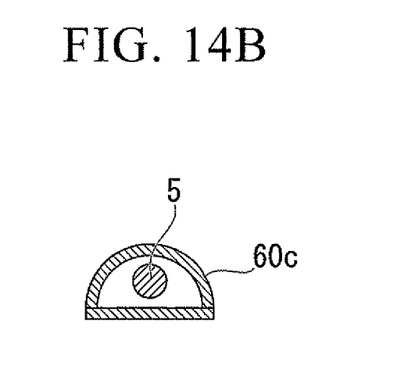
FIG. 14B is a cross-sectional view taken along a line C-C in FIG. 14A.

FIGS. 14A and 14B are cross-sectional views showing a fifth embodiment of the present invention.

A stabilizer (i.e., a wire restricting portion) 60 that is used in this fifth embodiment is provided with a pipe portion 60a through which a wire is inserted and thereby guided, a pipe fixing portion 60b that is provided on an outer circumference of the pipe portion 60a and that fixes the pipe portion 60a in a center portion of the insertion through hole 3a of the flexible sheath 3 in a position in the vicinity of the wire insertion through hole 61, and an inclined wire guide portion 60c which is connected to a distal end of the pipe portion 60a so as to be at a predetermined angle of inclination relative to the axis of this pipe portion 60a and is provided such that a distal end thereof is directed towards the wire insertion through hole 61. The inclined wire guide portion 60c may be formed in a semicircular pipe shape obtained by splitting the pipe in half lengthwise along its axial direction, or may be formed by bending an unmodified pipe. Moreover, the distal end of the inclined wire guide portion (i.e., guide portion) 60c may also be positioned so as to protrude to the outside of the wire insertion through hole 61.

In the treatment tool of this fifth embodiment is well, the same effects as in the treatment tool of the above described first embodiment are obtained.

Note that the present invention is not limited to the above described embodiments and suitable design modifications may be made thereto insofar as they do not depart from the spirit or scope of the invention.

For example, in the above described first embodiment, a stabilizer serving as a wire restricting portion is provided respectively for both the first wire insertion through hole 4a and the second wire insertion through hole 4b, however, the present invention is not limited to this and it is also possible for a stabilizer to be provided for just one of the wire insertion through holes.

Moreover, in each of the above described embodiments, a description is given using as an example an incision tool which incises a narrowing portion of an esophagus by expanding a plurality of wires radially outwards and then rotating these wires, however, the present invention is not limited to this and may also be applied to other treatment tools. It is also possible for the wire to have any one of a circular cross-section, an elliptical cross-section, and a rect-angular cross-section and the like, and the shape of the cross-section is not particularly restricted.

According to this treatment tool, when a portion of a wire which passes through a hole portion and is exposed to the outside of a flexible sheath is expanded, the wire restricting portion makes it possible to prevent this wire twisting or bending and being shifted away from the radial direction of the flexible sheath. Because of this the wire can be expanded to a desired shape.

According to this treatment tool, using a structure which is simple and which restricts movement of a wire which passes through a guide portion provided in a wire restricting portion, it is possible to reliably restrict movement of the wire. Moreover, because the structure involves simply mounting a new wire restricting portion on a flexible sheath, the present invention can also be applied to existing treatment tools without any large scale modifications being required.

According to this treatment tool, because an expanding wire does not become twisted or bent, the incision direction can be stabilized when an incision is being made using this incision knife, and the incision operation can be performed easily and in the desired location.

According to the present invention, a wire does not become twisted or bent when it is being expanded or rotated, so that it can be expanded to or held in a desired shape.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as limited by the foregoing description and is only limited by the scope of the appended claims.

What is claimed is:

1. A treatment tool that is used in conjunction with an endoscope comprising:
    a flexible sheath having a lumen which extends along an axial direction of the flexible sheath;
    a pair of hole portions placed on a distal end portion of the flexible sheath in the axial direction of the flexible sheath, the pair of hole portions penetrating the flexible sheath from the outside of the flexible sheath;
    a wire passed through the pair of hole portions and having an exposed portion which is exposed to the outside of the flexible sheath between the pair of hole portions and an un-exposed portion which is located inside the lumen of the flexible sheath, the exposed portion being configured to deform so as to expand outwardly or contract inwardly in a radial direction of the flexible sheath; and
    a wire restricting portion fixed to an inside of the lumen at the vicinity of at least one of the pair of hole portions in the lumen of the flexible sheath so as to prevent a relative movement of the wire restricting portion to the pair of hole portions, the wire restricting portion having a guide groove formed along the radial direction and a pair of wall portions positioned at both sides of the guide groove in the radial direction of the flexible sheath, wherein
    when the exposed portion of the wire is expanded outwardly in the radial direction of the sheath for treatment,
        the un-exposed portion of the wire is capable of being inserted into the guide groove,
        the un-exposed portion of the wire is capable of being in contact with the pair of wall portions,
        the guide groove is configured to allow both the exposed portion and the un-exposed portion to move in the radial direction of the flexible sheath with respect to the wire restricting portion, the pair of wall portions are configured to allow the exposed portion to move in a circumferential direction of the flexible sheath with respect to the wire restricting portion, and the pair of wall portions are further configured to prevent the un-exposed portion of the wire from moving in the circumferential direction of the flexible sheath with respect to the wire restricting portion.

2. The treatment tool according to claim 1, wherein the guide groove whose width is larger than an outer diameter of the wire is formed in the wire restricting portion, and the wire restricting portion is mounted on an inner wall portion of the lumen of the flexible sheath such that the wire which passes through the hole portion passes continuously through the guide groove.

3. The treatment tool according to claim 1, wherein the wire is an incision knife.

4. The treatment tool according to claim 1, wherein a plurality of the pairs of hole portions are formed on the distal end portion of the flexible sheath at equidistant intervals in the circumferential direction of the flexible sheath, and a plurality of the exposed portions of the wires are placed at equidistant angular intervals in the circumferential direction of the flexible sheath so as to radiate outwards.

5. The treatment tool according to claim 1, wherein the wire restricting portion has a circular plate portion, and a protruding portion extending from one side of the circular plate portion in a direction which is perpendicular to the circular plate portion, and the guide groove is formed by the circular plate portion and a pair of wall portions constituted of the one wall portion of each of the two protruding portions.

6. The treatment tool according to claim 1, wherein at least a portion of the wire restricting portion is located at a position which is overlapped with the hole portion.

7. The treatment tool according to claim 1, wherein the wire restricting portion is fixed in the lumen of the flexible sheath at the vicinity of an end part of at least one of the pair of hole portions in the axial direction, and at least a portion of the guide groove is located at a position so as to face to the hole portion.

\* \* \* \* \*